(12) United States Patent
Ammermann et al.

(10) Patent No.: US 10,645,930 B2
(45) Date of Patent: May 12, 2020

(54) FUNGICIDAL MIXTURES BASED ON PROTHIOCONAZOLE AND A STROBILURIN DERIVATIVE

(71) Applicant: BASF SE, Ludwigshafen (DE)

(72) Inventors: Eberhard Ammermann, Heppenheim (DE); Reinhard Stierl, Freinsheim (DE); Gisela Lorenz, Neustadt (DE); Siegfried Strathmann, Limburgerhof (DE); Klaus Schelberger, Gönnheim (DE); V. James Spadafora, Sugar Land, TX (US); Thomas Christen, Dannstadt-Schauernheim (DE)

(73) Assignee: BASF SE, Ludwigshafen (DE)

( * ) Notice: Subject to any disclaimer, the term of this patent is extended or adjusted under 35 U.S.C. 154(b) by 272 days.

(21) Appl. No.: 14/799,692

(22) Filed: Jul. 15, 2015

(65) Prior Publication Data
US 2015/0313227 A1 Nov. 5, 2015
US 2016/0143282 A2 May 26, 2016

Related U.S. Application Data

(63) Continuation of application No. 10/505,440, filed as application No. PCT/EP03/01929 on Feb. 26, 2003, now abandoned.

(30) Foreign Application Priority Data

Mar. 1, 2002 (DE) .................................. 102 08 838

(51) Int. Cl.
*A01N 43/653* (2006.01)
*A01N 43/40* (2006.01)
*A01N 43/56* (2006.01)
*C07D 249/12* (2006.01)
*A01N 47/24* (2006.01)
*A01N 37/50* (2006.01)
*A01N 37/18* (2006.01)

(52) U.S. Cl.
CPC .......... *A01N 43/653* (2013.01); *A01N 37/18* (2013.01); *A01N 37/50* (2013.01); *A01N 43/40* (2013.01); *A01N 43/56* (2013.01); *A01N 47/24* (2013.01); *C07D 249/12* (2013.01)

(58) Field of Classification Search
None
See application file for complete search history.

(56) References Cited

U.S. PATENT DOCUMENTS

| | | |
|---|---|---|
| 5,145,843 A | 9/1992 | Arnold et al. |
| 5,240,940 A | 8/1993 | Arnold et al. |
| 5,395,854 A | 3/1995 | Brand et al. |
| 5,516,804 A | 5/1996 | Brand et al. |
| 5,523,454 A | 6/1996 | Brand et al. |
| 5,677,347 A | 10/1997 | Brand et al. |
| 5,789,430 A | 8/1998 | Jautelat et al. |
| 5,859,039 A | 1/1999 | Jautelat et al. |
| 5,869,517 A | 2/1999 | Müller et al. |
| 5,948,932 A | 9/1999 | Grote et al. |
| 6,037,378 A | 3/2000 | Grote et al. |
| 6,054,592 A | 4/2000 | Müller et al. |
| 6,180,638 B1 | 1/2001 | Mueller et al. |
| 6,306,850 B1 | 10/2001 | Dutzmann et al. |
| 6,355,634 B1 | 3/2002 | Isenring et al. |
| 6,407,100 B1 | 6/2002 | Isenring et al. |
| 6,787,567 B2 | 9/2004 | Wachendorff-Neumann et al. |
| 6,797,301 B1 | 9/2004 | Duvert et al. |
| 7,186,672 B2 | 3/2007 | Mueller et al. |
| 2002/0173529 A1 | 11/2002 | Dutzmann et al. |
| 2006/0004070 A1 | 1/2006 | Wachendorff-Neumann et al. |

FOREIGN PATENT DOCUMENTS

| | | |
|---|---|---|
| CA | 2 367 361 A1 | 10/2001 |
| EP | 0 460 575 A | 12/1991 |
| EP | 0477631 B1 | 11/1995 |
| EP | 0804421 B1 | 9/1998 |
| EP | 0278595 A2 | 8/1999 |
| EP | 0793657 B1 | 5/2000 |
| EP | 0 876 332 A | 6/2001 |
| EP | 0326330 B1 | 7/2002 |
| WO | WO 96 16048 A | 5/1996 |
| WO | 9700012 A1 | 1/1997 |
| WO | 9740688 A1 | 11/1997 |
| WO | WO 98 47367 A | 10/1998 |
| WO | WO 00/47047 A1 | 8/2000 |
| WO | WO 00 63188 A | 10/2000 |

(Continued)

OTHER PUBLICATIONS

Wong et al. "Distribution of Baseline Sensitivities to Azoxystrobin Among Isolates of Plasmopara viticola", The American Phytopathological Society, vol. 84 No. 3, (2000), pp. 275-281.
English translation of BASF Reply to Administrative Brazilian Nullity Request of Application No. 0307729—dated Feb. 12, 2016.
C.D.S. Tomlin, ed., The Pesticide Manual, 11th ed. (1997), pp. 1242-1245; pub. by British Crop Protection Council (UK).
C.D.S. Tomlin, ed., The Pesticide Manual, 15th ed. (2009), pp. 965-966, 1033-1034; pub. by British Crop Protection Council (UK).
C.D.S. Tomlin, ed., The Pesticide Manual, 13th ed. (2003), p. 892; pub. by British Crop Protection Council (UK).
Data sheets from the Compendium of Pesticide Common Names; http://www.alanwood.net/pesticides/kresoxim-methyl.html; http://www.alanwood.net/pesticides/azoxystrobin.html; http://www.alanwood.net/pesticides/metominostrobin.html (accessed Aug. 4, 2009).

(Continued)

*Primary Examiner* — Kyle A Purdy
(74) *Attorney, Agent, or Firm* — McBee Moore & Vanik IP, LLC

(57) ABSTRACT

Disclosed is a fungicidal mixture containing (1) 2-[2-(1-chlorocyclopropyl)-3-(2-chlorophenyl)-2-hydroxypropyl]-2,4-dihydro[1,2,4]-triazole-3-thion of formula (I) or the salts or adducts thereof, and at least one additional fungicidal compound or the salts or adducts thereof, selected among (2) trifloxystrobin of formula (II), (3) picoxystrobin of formula (III), (4) pyraclostrobin of formula (IV), (5) dimoxystrobin of formula (V), and (6) a strobilurin derivative of formula (VI), in a synergistically active quantity.

16 Claims, No Drawings

(56) References Cited

FOREIGN PATENT DOCUMENTS

| WO | 02056686 A1 | 7/2002 |
| WO | 2004000021 A1 | 12/2003 |
| WO | WO 2004/000021 A1 | 12/2003 |

OTHER PUBLICATIONS

Mode of Action of Fungicides, FRAC classification on mode of action; Mode of Action Poster (www.frac.info) (Jun. 2009).

Research Disclosure 41512: Fungicidal Compositions; Research Disclosure Journal (disclosed anonymously) (Nov. 1998), pp. 1436-1439; Kenneth Mason Publications Ltd.

Research Disclosure 405085: Strobilurin Compositions; Research Disclosure Journal (disclosed anonymously) Jan. 1998), pp. 2-8; Kenneth Mason Publications Ltd.

Research Disclosure 429035: Picoxystrobin Compositions; Research Disclosure Journal (disclosed anonymously) Jan. 2000), pp. 2-7; Kenneth Mason Publications Ltd.

K.W. Jayasena et al., Evaluation of fungicides in control of spot-type net blotch on barley, Crop Protection 21 (2002), pp. 63-69.

S.R. Colby, Calculating synergistic and antagonistic responses of herbicide combinations, Weeds 15 (1967), pp. 20-22.

D.W. Bartlett et al., Understanding the strobilurin fungicides, Pesticide Outlook (Aug. 2001), pp. 143-148.

T.R. Roberts et al., eds., Metabolic Pathways of Agrochemicals, Part 2: Insecticides and Fungicides, "Azoles and Analogues" (1999), pp. 1011-1013; pub. by Royal Society of Chemistry (UK).

FUNGICIDAL MIXTURES BASED ON PROTHIOCONAZOLE AND A STROBILURIN DERIVATIVE

This application is a continuation of U.S. Ser. No. 10/505,440, filed Aug. 24, 2004, which is a 35 U.S.C. 371 National Phase Entry Application from PCT/EP03/01929, filed Feb. 26, 2003, which claims the benefit of German Patent Application No. 10208838.1 filed on Mar. 1, 2002, the disclosures of which are incorporated herein in their entireties by reference.

The present invention relates to a fungicidal mixture, comprising (1) 2-[2-(1-chlorocyclopropyl)-3-(2-chlorophenyl)-2-hydroxypropyl]-2,4-dihydro-[1,2,4]-triazole-3-thione (prothioconazole) of the formula I or its salts or adducts

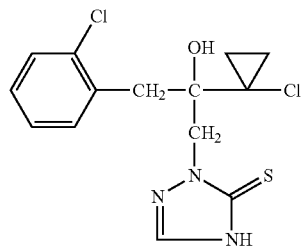

(I)

and at least one further fungicidal compound or its salts or adducts, selected from the group consisting of (2) trifloxystrobin of the formula II

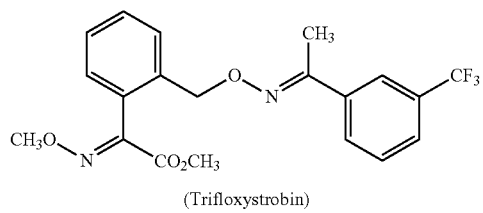

(Trifloxystrobin)

and
(3) picoxystrobin of the formula III

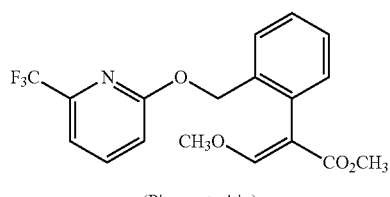

(Picoxystrobin)

and
(4) pyraclostrobin of the formula IV

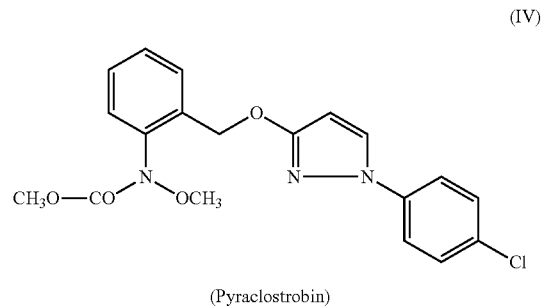

(Pyraclostrobin)

and
(5) dimoxystrobin of the formula V

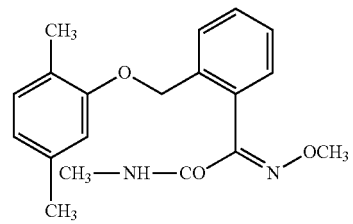

(Dimoxystrobin)

and
(6) a strobilurin derivative of the formula VI (VI)

in a synergistically effective amount.

Moreover, the invention relates to a method for controlling harmful fungi using mixtures of the compounds I with at least one of the compounds II, III, IV, V or VI, and to the use of the compounds I, II, III, IV, V and VI for preparing such mixtures, and to compositions comprising such mixtures.

The compound of the formula I, 2-[2-(1-chlorocyclopropyl)-3-(2-chlorophenyl)-2-hydroxypropyl]-2,4-dihydro-[1,2,4]-triazole-3-thione (prothioconazole), has already been disclosed in WO 96/16048.

A number of active compound combinations of prothioconazole with a large number of other fungicidal compounds have been disclosed in WO 98/47367.

Trifloxystrobin of the formula II and its use as crop protection agent are described in EP-A-0 460 575.

Picoxystrobin has been disclosed in EP-A-0 326 330.

The strobilurin derivative of the formula IV is likewise already known and has been described in EP-A-0 804 421.

The strobilurin derivative of the formula V has been disclosed in EP-A-0 477 631.

Finally, the strobilurin derivative of the formula VI is likewise known and has been described in EP-A-0 876 332.

It is an object of the present invention to provide mixtures which have further improved activity against harmful fungi combined with a reduced total amount of active compounds applied (synergistic mixtures), with a view to reducing the application rates and improving the activity spectrum of the known compounds I, II, III, IV, V and VI.

We have found that this object is achieved by the mixture, defined at the outset, of prothioconazole with at least one strobilurin derivative. Moreover, we have found that applying the compound I and at least one of the compounds II, III, IV, V or VI simultaneously, i.e. together or separately, or applying the compound I and at least one of the compounds II, III, IV, V or VI in succession provides better control of harmful fungi than is possible with the individual compounds alone.

2-[2-(1-Chlorocyclopropyl)-3-(2-chlorophenyl)-2-hydroxypropyl]-2,4-dihydro-[1,2,4]-triazole-3-thione of the formula I is known from WO 96-16 048. The compound can be present in the "thiono" form of the formula

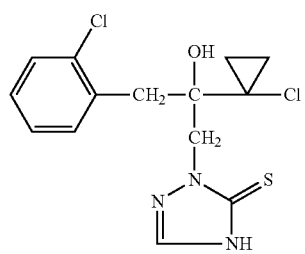

(I)

or in the tautomeric "mercapto" form of the formula

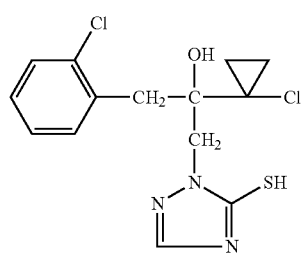

(Ia)

For the sake of simplicity, only the "thiono" form is shown in each case.

Trifloxystrobin of the formula II

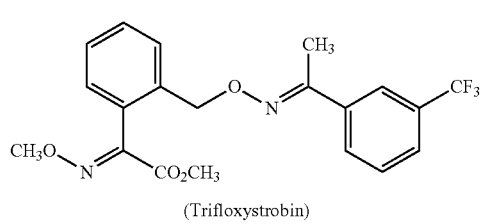

(II)

(Trifloxystrobin)

is known from EP-A 0 460 572.

Picoxystrobin of the formula III

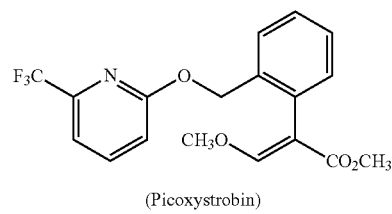

(III)

(Picoxystrobin)

is known from EP-A-0 326 330.

Pyraclostrobin of the formula IV

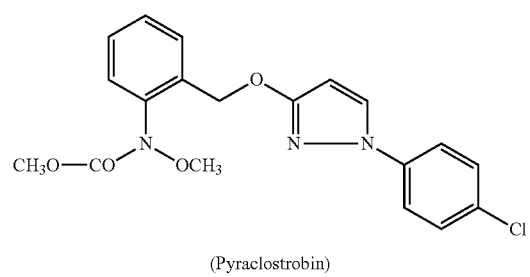

(IV)

(Pyraclostrobin)

is known from EP-A 0 804 421.

Dimoxystrobin of the formula V

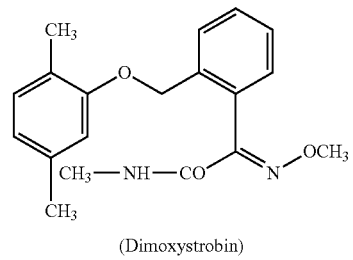

(V)

(Dimoxystrobin)

is known from EP-A 0 477 631.

The strobilurin derivative of the formula VI

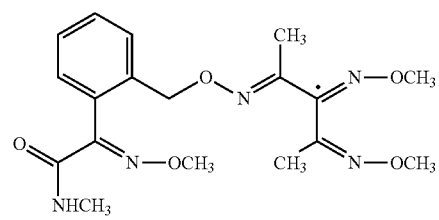

(VI)

is known from EP-A 0 876 332.

Owing to the basic character of their nitrogen atoms, the compounds I to VI are capable of forming salts or adducts with inorganic or organic acids or with metal ions.

Examples of inorganic acids are hydrohalic acids, carbonic acid, such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, for example p-toluenesulfonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminum, tin and lead, and of the first to eighth transition group, in particular chromium, manganese, iron, cobalt, nickel, copper, zinc and others. Particular preference is given to the metal ions of the elements of the transition groups of the fourth period. The metals can be present in the various valencies that they can assume.

Preference is given to mixtures of prothioconazole with trifloxystrobin of the formula II.

Preference is also given to mixtures of prothioconazole with picoxystrobin of the formula III.

Preference is given to mixtures of prothioconazole with pyraclostrobin of the formula IV.

Preference is furthermore also given to mixtures of prothioconazole with dimoxystrobin of the formula V.

Preference is also given to mixtures of prothioconazole with the strobilurin derivative of the formula VI.

Preference is also given to three-component mixtures of prothioconazole with two of the abovementioned strobilurin derivatives.

When preparing the mixtures, it is preferred to employ the pure active compounds I, II, III, IV, V and VI, to which may be added further active compounds against harmful fungi or other pests, such as insects, arachnids or nematodes, or else herbicidal or growth-regulating active compounds or fertilizers.

The mixtures of the compound I with at least one of the compounds II, III, IV, V or VI or the compound I, used simultaneously, jointly or separately, with at least one of the compounds II, III, IV, V or VI exhibit outstanding activity against a wide range of phytopathogenic fungi, in particular from the classes of the Ascomycetes, Basidiomycetes, Phycomycetes and Deuteromycetes. Some of them act systemically and can therefore also be employed as folio- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, corn, fruit species, rice, rye, soya, grapevine, wheat, ornamentals, sugar cane, and a variety of seeds.

They are particularly suitable for controlling the following phytopathogenic fungi: *Blumeria graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and *Fusarium* and *Verticillium* species.

They can furthermore be employed in the protection of materials (e.g. the protection of wood), for example against *Paecilomyces variotii*.

The compound I can be applied simultaneously, that is either together or separately, or successively with at least one of the compounds II, III, IV, V and VI, the sequence, in the case of separate application, generally not having any effect on the result of the control measures.

The compounds I and II are usually applied in a weight ratio of from 20:1 to 1:20, in particular from 10:1 to 1:10, preferably from 5:1 to 1:5.

The compounds I and III are usually applied in a weight ratio of from 20:1 to 1:20, in particular from 10:1 to 1:10, preferably from 5:1 to 1:5.

The compounds I and IV are usually applied in a weight ratio of from 20:1 to 1:20, in particular from 10:1 to 1:10, preferably from 5:1 to 1:5.

The compounds I and V are usually applied in a weight ratio of from 20:1 to 1:20, in particular from 10:1 to 1:10, preferably from 5:1 to 1:5.

The compounds I and VI are usually applied in a weight ratio of from 20:1 to 1:20, in particular from 10:1 to 1:10, preferably from 5:1 to 1:5.

Depending on the kind of effect desired, the application rates of the mixtures according to the invention are, in particular in agricultural crop areas, from 0.01 to 8 kg/ha, preferably from 0.1 to 5 kg/ha, in particular from 0.1 to 3.0 kg/ha.

The application rates for the compound I are from 0.01 to 1 kg/ha, preferably from 0.05 to 0.5 kg/ha, in particular from 0.05 to 0.3 kg/ha.

Correspondingly, in the case of the compound II, the application rates are from 0.01 to 1 kg/ha, preferably from 0.02 to 0.5 kg/ha, in particular from 0.05 to 0.3 kg/ha.

Correspondingly, in the case of the compound III, the application rates are from 0.01 to 1 kg/ha, preferably from 0.02 to 0.5 kg/ha, in particular from 0.05 to 0.3 kg/ha.

Correspondingly, in the case of the compound IV, the application rates are from 0.01 to 1 kg/ha, preferably from 0.02 to 0.5 kg/ha, in particular from 0.05 to 0.3 kg/ha.

Correspondingly, in the case of the compound V, the application rates are from 0.01 to 1 kg/ha, preferably from 0.02 to 0.5 kg/ha, in particular from 0.05 to 0.3 kg/ha.

Correspondingly, in the case of the compound VI, the application rates are from 0.01 to 1 kg/ha, preferably from 0.02 to 0.5 kg/ha, in particular from 0.05 to 0.3 kg/ha.

For seed treatment, the application rates of the mixture are generally from 0.001 to 250 g/kg of seed, preferably from 0.01 to 100 g/kg of seed, in particular from 0.01 to 50 g/kg.

If phytopathogenic harmful fungi are to be controlled, the separate or joint application of the compound I with at least one of the compounds II, III, IV, V and VI or of the mixtures of the compound I with at least one of the compounds II, III, IV, V or VI is effected by spraying or dusting the seeds, the plants or the soils before or after sowing of the plants, or before or after plant emergence.

The fungicidal synergistic mixtures according to the invention or the compound I and at least one of the compounds II, III, IV, V and VI can be formulated, for example, in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in each case, it should ensure as fine and uniform as possible a distribution of the mixture according to the invention.

The formulations are prepared in a known manner, for example by adding solvents and/or carriers. Usually, inert additives, such as emulsifiers or dispersants, are added to the formulations.

Suitable surfactants are the alkali metal salts, alkaline earth metal salts and ammonium salts of aromatic sulfonic acids, for example ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenyl ether, ethoxylated isooctyl-, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compound I and at least one of the compounds II, III, IV, V and VI or the mixture of the compound I with at least one compound II, III, IV, V or VI with a solid carrier.

Granules (for example coated granules, impregnated granules or homogeneous granules) are usually prepared by binding the active compound, or active compounds, to a solid carrier.

Fillers or solid carriers are, for example, mineral earths such as silica gel, silicas, silicates, talc, kaolin, limestone, lime, chalk, bole, loess, clay, dolomite, diatomaceous earth, calcium sulfate, magnesium sulfate, magnesium oxide, ground synthetic materials, and also fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably from 0.5 to 90% by weight, of the compound I and at least one of the compounds II, III, IV, V or VI or of the mixture of the compound I with at least one compound II, III, IV, V or VI. The active compounds are employed in a purity of from 90% to 100%, preferably 95% to 100% (according to NMR spectrum or HPLC).

The compound I and at least one of the compounds II, III, IV, V and VI or the mixtures or the corresponding formulations are applied by treating the harmful fungi, their habitat, or the plants, seeds, soils, areas, materials or spaces to be kept free from them with a fungicidally effective amount of the mixture, or of the compound I and at least one of the compounds II, III, IV, V or VI in the case of separate application.

Application can be effected before or after infection by the harmful fungi.

USE EXAMPLE

The synergistic activity of the mixtures according to the invention could be demonstrated by the following experiments:

The active compounds, separately or together, were formulated as a 10% emulsion in a mixture of 63% by weight of cyclohexanone and 27% by weight of emulsifier, and diluted with water to the desired concentration.

Evaluation was carried out by determining the infected leaf areas in percent. These percentages were converted into efficacies. The efficacy (W) was determined as follows using Abbot's formula:

$$W = \left(1 - \frac{\alpha}{\beta}\right) * 100$$

α corresponds to the fungal infection of the treated plants in % and
β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

$E = x+y-x\cdot y/100$  Colby's formula:

E expected efficacy, expressed in % of the untreated control, when using the mixture of the active compounds A and B at the concentrations a and b
x efficacy, expressed in % of the untreated control, when using the active compound A at the concentration a
y efficacy, expressed in % of the untreated control, when using the active compound B at the concentration b Use Example 1: Activity Against Mildew of Wheat Caused by *Erysiphe* [syn. *Blumeria*]*graminis* forma specialis. *tritici*

Leaves of wheat seedlings of the cultivar "Kanzler" grown in pots were sprayed to runoff point with an aqueous preparation of active compound which had been prepared from a stock solution comprising 10% of active compound, 85% of cyclohexanone. and 5% of emulsifier, and, 24 hours after the spray coating had dried on, the leaves were dusted with spores of mildew of wheat (*Erysiphe* [syn. *Blumeria*] *graminis* forma specialis. *tritici*). The test plants were then placed in a greenhouse at 20-24° C. and 60-90% relative atmospheric humidity. After 7 days, the extent of the development of the mildew was determined visually in % infection of the entire leaf area.

The visually determined values for the percentage of diseased leaf areas were converted into efficacies as % of the untreated control. An efficacy of 0 means the same disease level as in the untreated control, an efficacy of 100 means a disease level of 0%. The expected efficacies for the active compound combinations were determined using Colby's formula mentioned above and compared with the observed efficacies.

TABLE 1

| Active compound | Concentration of active compound in the spray liquor in ppm | Efficacy in % of the untreated control |
|---|---|---|
| Control (untreated) | (90% infected) | 0 |
| Compound I = prothioconazole | 4 | 22 |
|  | 1 | 0 |
|  | 0.25 | 0 |
|  | 0.06 | 0 |
|  | 0.015 | 0 |
| Compound II = trifloxystrobin | 4 | 83 |
|  | 1 | 44 |
|  | 0.25 | 22 |
|  | 0.06 | 0 |
| Compound III = picoxystrobin | 0.25 | 11 |
| Compound IV = pyraclostrobin | 1 | 0 |
|  | 0.25 | 0 |

TABLE 2

| Combinations according to the invention | Observed efficacy | Calculated efficacy*) |
|---|---|---|
| Compound I = prothioconazole + Compound II = trifloxystrobin 0.015 + 0.25 ppm Mixture 1:16 | 33 | 22 |
| Compound I = prothioconazole + Compound II = trifloxystrobin 1:4 ppm Mixture 1:4 | 94 | 83 |
| Compound I = prothioconazole + Compound II = trifloxystrobin 0.25 + 1 ppm Mixture 1:4 | 56 | 44 |
| Compound I = prothioconazole + Compound II = trifloxystrobin 0.25 + 0.06 ppm Mixture 4:1 | 22 | 0 |
| Compound I = prothioconazole + Compound II = trifloxystrobin 4 + 0.25 ppm Mixture 16:1 | 55 | 40 |
| Compound I = prothioconazole + Compound III = picoxystrobin 0.06 + 0.25 ppm Mixture 1:4 | 33 | 11 |
| Compound I = prothioconazole + Compound III = picoxystrobin 1 + 0.25 ppm Mixture 4:1 | 22 | 11 |
| Compound I = prothioconazole + Compound IV = pyraclostrobin 0.06 + 1 ppm Mixture 1:16 | 33 | 0 |
| Compound I = prothioconazole + Compound IV = pyraclostrobin 0.015 + 0.25 ppm Mixture 1:16 | 33 | 0 |
| Compound I = prothioconazole + Compound IV = pyraclostrobin 0.25 + 1 ppm Mixture 1:4 | 33 | 0 |
| Compound I = prothioconazole + Compound IV = pyraclostrobin 0.06 + 0.25 ppm Mixture 1:4 | 22 | 0 |
| Compound I = prothioconazole + Compound IV = pyraclostrobin 4 + 1 ppm Mixture 4:1 | 33 | 22 |

*)efficacy calculated using Colby's formula

The test results show that in all mixing ratios the observed efficacy is higher than the efficacy calculated beforehand using Colby's formula (from Synerg 171. XLS).

Use Example 2: Curative Activity Against Brown Rust of Wheat Caused by *Puccinia recondita*

Leaves of wheat seedlings of the cultivar "Kanzler" grown in pots were dusted with spores of brown rust (*Puccinia recondita*). The pots were then placed in a chamber with high atmospheric humidity (90-95%), at 20-22° C. for 24 hours. During this time, the spores germinated and the germinal tubes penetrated into the leaf tissue. The next day, the infected plants were sprayed to runoff point with an aqueous formulation of active compound prepared from a stock solution comprising 10% of active compound, 85% of cyclohexanone and 5% of emulsifier. After the spray coating had dried on, the test plants were cultivated in a greenhouse at 20-22° C. and 65-70% relative atmospheric humidity for 7 days. Thereafter, the extent of the rust fungus development on the leaves was determined.

The visually determined values for the percentage of diseased leaf areas were converted into efficacies as % of the untreated control. An efficacy of 0 means the same disease level as in the untreated control, an efficacy of 100 means a disease level of 0%. The expected efficacies for the combinations of active compounds were determined using Colby's formula mentioned above and compared with the observed efficacies.

TABLE 3

| Active compound | Concentration of active compound in the spray liquor in ppm | Efficacy in % of the untreated control |
|---|---|---|
| Control (untreated) | (90% infected) | 0 |
| Compound I = prothioconazole | 1 | 0 |
|  | 0.25 | 0 |
|  | 0.015 | 0 |
|  | 0.006 | 0 |
| Compound II = trifloxystrobin | 0.25 | 0 |
|  | 0.06 | 0 |
| Compound III = picoxystrobin | 1 | 33 |
|  | 0.25 | 0 |
|  | 0.06 | 0 |
| Compound IV = pyraclostrobin | 0.25 | 0 |
|  | 0.06 | 0 |

TABLE 4

| Combinations according to the invention | Observed efficacy | Calculated efficacy*) |
|---|---|---|
| Compound I = prothioconazole + Compound II = trifloxystrobin 0.015 + 0.25 ppm Mixture 1:16 | 22 | 0 |
| Compound I = prothioconazole + Compound II = trifloxystrobin 0.06:0.25 ppm Mixture 1:4 | 22 | 0 |
| Compound I = prothioconazole + Compound II = trifloxystrobin 1 + 0.25 ppm Mixture 4:1 | 67 | 0 |
| Compound I = prothioconazole + Compound II = trifloxystrobin 0.25 + 0.06 ppm Mixture 4:1 | 67 | 0 |
| Compound I = prothioconazole + Compound II = trifloxystrobin 1 + 0.06 ppm Mixture 16:1 | 11 | 0 |
| Compound I = prothioconazole + Compound III = picoxystrobin 0.06 + 1 ppm Mixture 1:16 | 44 | 33 |
| Compound I = prothioconazole + Compound III = picoxystrobin 0.06 + 0.25 ppm Mixture 1:4 | 11 | 0 |
| Compound I = prothioconazole + Compound III = picoxystrobin 1 + 0.25 ppm Mixture 4:1 | 78 | 0 |
| Compound I = prothioconazole + Compound III = picoxystrobin 0.25 + 0.06 ppm Mixture 4:1 | 78 | 0 |

TABLE 4-continued

| Combinations according to the invention | Observed efficacy | Calculated efficacy*) |
|---|---|---|
| Compound I = prothioconazole + Compound III = picoxystrobin 1 + 0.06 ppm Mixture 16:1 | 44 | 0 |
| Compound I = prothioconazole + Compound IV = pyraclostrobin 0.015 + 0.25 ppm Mixture 1:16 | 94 | 0 |
| Compound I = prothioconazole + Compound IV = pyraclostrobin 0.06 + 0.25 ppm Mixture 1:4 | 89 | 0 |
| Compound I = prothioconazole + Compound IV = pyraclostrobin 1 + 0.25 ppm Mixture 4:1 | 22 | 0 |
| Compound I = prothioconazole + Compound IV = pyraclostrobin 0.25 + 0.06 ppm Mixture 4:1 | 22 | 0 |
| Compound I = prothioconazole + Compound IV = pyraclostrobin 1 + 0.06 ppm Mixture 16:1 | 89 | 0 |

*)efficacy calculated using Colby's formula

The test results show that in all mixing ratios the observed efficacy is higher than the efficacy calculated beforehand using Colby's formula (from Synerg 171. XLS).

The invention claimed is:

1. A fungicidal mixture comprising (i) prothioconazole and/or a salt or adduct thereof, and (ii) trifloxystrobin and/or a salt and/or adduct thereof, in a synergistically effective amount and wherein the weight ratio of prothioconazole and/or salt and/or adduct to trifloxystrobin and/or salt and/or adduct is from 10:1 to 1:10.

2. A fungicidal mixture of claim 1, wherein the weight ratio of prothioconazole and/or salt and/or adduct to trifloxystrobin and/or salt and/or adduct is from 5:1 to 1:5.

3. A method for controlling harmful fungi and/or a habitat thereof and/or one or more plants, seeds, soils, areas materials or spaces desired to be kept free from said harmful fungi, said method comprising treating with (i) prothioconazole and/or a salt or adduct thereof and (ii) trifloxystrobin and/or a salt and/or adduct thereof in a synergistically effective amount, and wherein the weight ratio of prothioconazole and/or salt and/or adduct to trifloxystrobin and/or salt and/or adduct is from 10:1 to 1:10.

4. A method of claim 3, wherein said prothioconazole and/or salt and/or adduct and said trifloxystrobin and/or salt and/or adduct are applied simultaneously, separately, and/or in succession.

5. A method of claim 3, wherein said prothioconazole and/or salt and/or adduct and said trifloxystrobin and/or salt and/or adduct is/are applied in an amount of from 0.01 to 8 kg/ha.

6. A fungicidal composition comprising the fungicidal mixture as claimed in claim 1 and a solid or liquid carrier.

7. A method for controlling harmful fungi and/or a habitat thereof and/or one or more plants, seeds, soils, areas materials or spaces desired to be kept free from said harmful fungi, said method comprising treating with the fungicidal composition as claimed in claim 6.

8. A fungicidal mixture wherein active compounds in said mixture consists of (i) prothioconazole and/or a salt or adduct thereof, and (ii) trifloxystrobin and/or a salt and/or adduct thereof in a synergistically effective amount and wherein the weight ratio of prothioconazole and/or salt and/or adduct to trifloxystrobin and/or salt and/or adduct is from 10:1 to 1:10.

9. A method of claim 3, wherein fungi in wheat are controlled.

10. A method of claim 3, wherein fungi in corn are controlled.

11. A method of claim 3, wherein fungi in soya are controlled.

12. A method of claim 3, wherein fungi in cotton are controlled.

13. A method of claim 3, wherein fungi in barley are controlled.

14. A method of claim 3, wherein fungi in oats are controlled.

15. A method of claim 3, wherein said prothioconazole and/or salt and/or adduct and said trifloxystrobin and/or salt and/or adduct is/are applied in an amount of from 0.1-5 kg/ha.

16. A method of claim 3, wherein said prothioconazole and/or salt and/or adduct and said trifloxystrobin and/or salt and/or adduct is/are applied in an amount of from 0.1-3.0 kg/ha.

* * * * *